Figure 1:
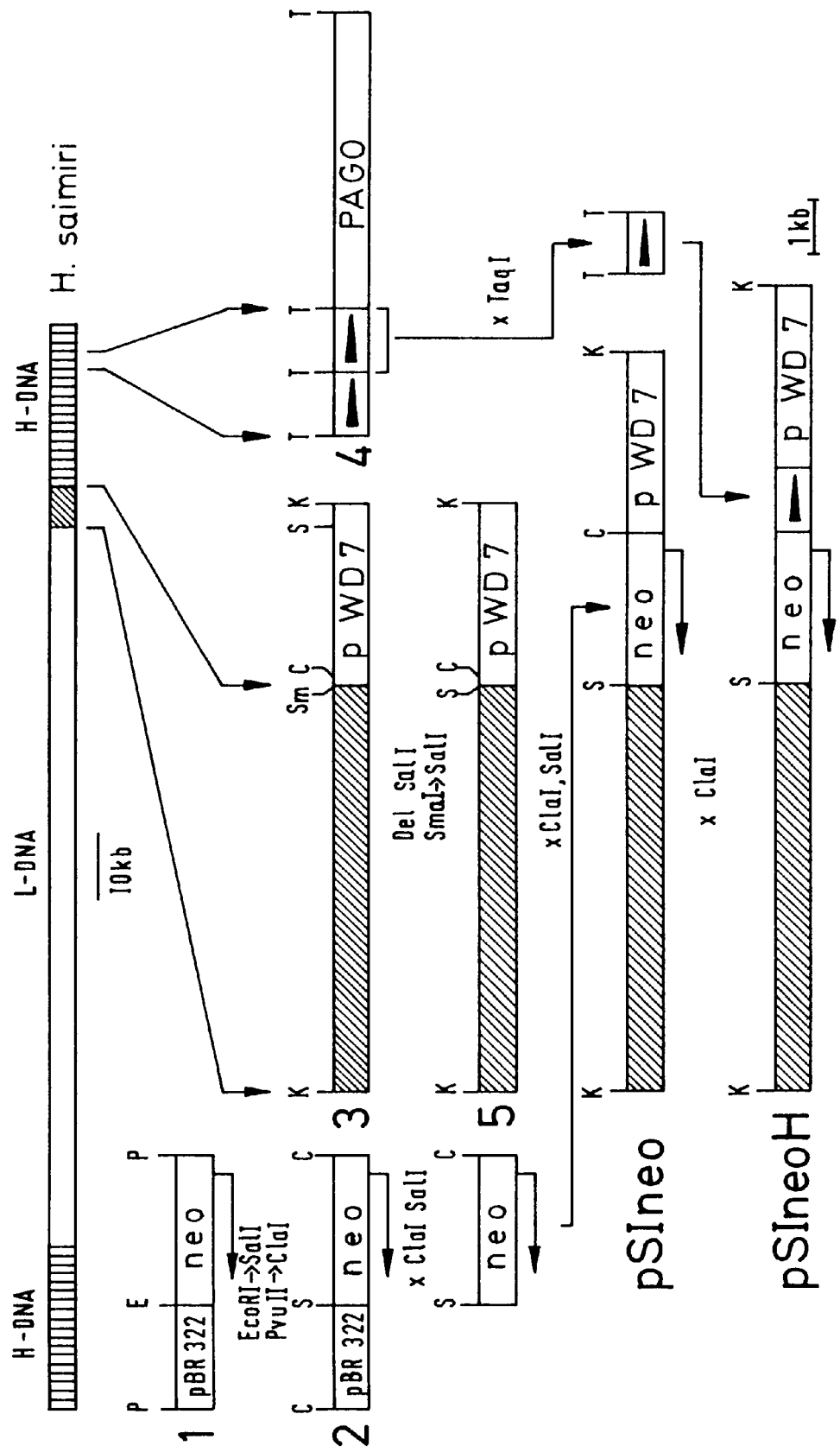

United States Patent [19]
Fleckenstein et al.

[11] Patent Number: 6,025,153
[45] Date of Patent: Feb. 15, 2000

[54] SELECTABLE VECTORS FOR HUMAN T CELLS

[75] Inventors: Bernhard Fleckenstein, Wiesenthau; Ralph Grassmann, Erlangen, both of Germany

[73] Assignee: Hoechst AG, Frankfurt am Main, Germany

[21] Appl. No.: 07/946,787

[22] Filed: Sep. 18, 1992

Related U.S. Application Data

[63] Continuation of application No. 07/417,596, Oct. 5, 1989, abandoned.

[30] Foreign Application Priority Data

Oct. 7, 1988 [DE] Germany .............................. 38 34 157

[51] Int. Cl.⁷ .......................... C12P 21/00; C12N 15/86; C12N 15/64
[52] U.S. Cl. .................. 435/69.1; 435/91.4; 435/91.41; 435/320.1; 435/366; 435/372; 435/372.3; 435/455; 435/456; 435/462; 435/463
[58] Field of Search ................................ 435/69.1, 172.3, 435/240.2, 320.1, 91.4, 91.41, 366, 372, 372.3, 455, 456, 462, 463; 536/23.1, 23.72

[56] References Cited

FOREIGN PATENT DOCUMENTS

WO 90/04020  4/1990  WIPO .

OTHER PUBLICATIONS

Fleckenstein et al., *The Herpesviruses*, v. 1, B. Roizman, ed., 1982, Plenum Publishing Co., New York.
Desrosiers et al., J. Virol 49(2):343–348 (1984).
Grassman and Fleckenstein, J. Virol. 63(4):1818–1821 (Apr. 1989).
Grassman et al., Proc. Nat'l Acad. Sci. USA 86:3351–3355 (May 1989).
Southern and Berg, J. Mol. and App. Gen. 1:327–341 (1982), Transformation of Mammalian Cells to Antibiotic Resistance with a Bacterial Gene Under Control of the SV40 Early Region Promoter.
Desrosiers et al., Mol. and Cell. Biol. 5(10) 2796–2803 (1985), Synthesis of Bovine Growth Hormone in Primates by Using a Herpesvirus Vector.
Schneider et al., Int. J. Cancer 19:621–26 (1977), Characterization of EBV–Genome Negative "Null" and "T" Cell Lines Derived From Children With Acute Lymphoblastic Leukemia and Leukemic Transformed Non–Hodgkin Lymphoma.
Fleckenstein et al., J. Virol. 15(2) 398–406 (1975), Repetitive Sequences in Complete and Defective Genomes of *Herpesvirus saimiri*.
Bankier, et al., J. Virol. 55(1) 133–39 (1985), Terminal Repetitive Sequences in *Herpesvirus saimiri* Virion DNA.
Graham and Van Der Eb, Virology 52:456–67 (1973), A New Technique for the Assay of Infectivity of Human Adenovirus 5 DNA.
Knust et al., Gene 25:281–89 (1983), Cloning of *Herpesvirus saimiri* DNA fragments representing the entire L–region of the genome.

*Primary Examiner*—David Guzo
*Attorney, Agent, or Firm*—Finnegan, Henderson, Farabow, Garrett & Dunner, L.L.P.

[57] ABSTRACT

Selectable *Herpesvirus saimiri* vectors which have a selection gene inserted into a junction region of the L- and H-DNA are described. Vectors of this type are able persistently to infect human T cells and thus are suitable for the expression of foreign genes in human T cells. An additional advantage is that no infectious virus particles are produced during this.

14 Claims, 3 Drawing Sheets

SELECTABLE VECTORS FOR HUMAN T CELLS

This application is a continuation of application Ser. No. 07/417,596, filed Oct. 5, 1989, now abandoned.

The invention relates to selectable vectors which make it possible to express foreign genes in human T cells.

Viruses of the herpes group (herpes simplex virus, cytomegalovirus, varicella/zoster virus or Herpesvirus suis) have been used successfully to express heterologous genes in monolayer cell cultures which have undergone lytic infection. However, there are no cell lines which are persistently infected by these viruses for an extended period. Persisting vectors have been constructed from the genome of Epstein-Barr virus (EBV), but it has not been possible to obtain infectious cell-free viruses from the infected B lymphocytes.

It has likewise been disclosed that *Herpesvirus (H.) saimiri* both multiplies lytically in epitheloid cells and persistently infects T cells from marmosets. The genome of *H. saimiri* is composed of a region of about 112 kb of a unique DNA of low GC content (L-DNA). It is flanked at both ends by a variable number of non-coding repeat units (H-DNA) which are arranged in tandem fashion and which each have a length of about 1.4 kb and are GC rich. *H. saimiri* induces rapidly growing T-cell lymphomas in some new-world primates and is able to transform marmoset T lymphocytes in vitro to permanent growth.

We have found that a recombinant *H. saimiri* virus which contains the neo gene is selected in high number in monkey kidney cell lines by geneticin (G418). The conditions for homologous recombination were chosen such that the neo gene, which represents here an example of any desired selectable gene, is inserted into the right junction site of the H- and L-DNA. These recombinants are able persistently to infect human T cell lines, with the viral DNA being in the form of an episome. Since the viral genome contains about 30% of highly repetitive DNA which can be replaced by heterologous DNA, vectors for the expression of foreign genes in human T cells are thus available.

It is furthermore regarded as an advantage of such expression systems that persistently infected cells, being non-producer cells, do not produce infectious virus particles. It is also possible to use replication-competent, non-oncogenic variants of *H. saimiri* as starting strains. These virus strains have deletions in the left-terminal L-DNA (B. Fleckenstein and R. Desrosiers (1982, "The Herpes viruses", Vol. 1, B. Roizman (ed.). Plenum Publishing Co., New York).

It has not hitherto been shown that *H. saimiri* infects human lymphatic cells.

Consequently, the invention relates to:
a) selectable *H. saimiri* recombinants which have a selection gene inserted in the right or left junction site or junction region of the H- and L-DNA,
b) a process for the preparation of the recombinants specified under a) and
c) the use thereof for the expression of foreign genes in human T lymphocytes, as well as
d) the generation of monkey T cell lines which constitutively express a foreign gene by means of transformation-competent recombinant *H. saimiri*.

Furthermore, the invention is detailed further in the patent claims and the examples.

EXAMPLE 1

Construction of plasmid pSIneo and pSINneoH pSIneo and pSIneoH were constructed in such a way that the homologous recombination with *H. saimiri* DNA results in no viral gene being deleted and no functional unit being interrupted.

The "neo" gene codes for a phosphotransferase which makes it possible to bypass the translation block induced by geneticin (G 418) in most eukaryotic cells.

The plasmid pSV2 neo (P. J. Southern and P. Berg (1982) J. Mol. Appl. Genetics, 327–341, Raven Press, New York) contains the neo gene under the transcription control of Sv40 elements (early promoter/enhancer, T antigen, mRNA splice signal and polyadenylation sites). The "neo" transcription unit was cut out of pSV2 neo, and the restriction cleavage site ends were converted by standard methods from PvuII into ClaI and from EcoRI into SalI ends. The cloning of the KpnI/SmaI fragment E, which has a length of about 9 kb and forms the right end of the L-DNA, has been described by KNUST (E. Knust et al. (1983) Gene 25, 281–289).

The cloning vector pWD7 with the said fragment E, used therein and called pWD11 (vector 3 herein), was converted by standard methods into vector 5 in such a way that the internal SalI site in pWD7 is deleted, and the SmaI site at the fragment E/pWD7 junction is mutated into a SalI site. The SmaI or SalI cleavage site is 35 nucleotides away from the end of the L-DNA in the first H repetition unit. After (5) has been cut with SalI and ClaI it is possible for the neo gene to be ligated in between fragment E and pWD7 in vector (5) to give the plasmid pSIneo. An H-DNA repetition unit of 1444 base pairs (bp) is finally, after cleavage with TaqI, placed between the neo and pWD7 portions so that the final result is the plasmid pSIneoH. The H-DNA repetition unit was obtained as the TaqI fragment from pFG24 (A. T. Bankier et al. (1985) J. Virol. 55, 133–139). The abovementioned synthetic steps are summarized in FIG. 1.

EXAMPLE 2

Cotransfection of linearized pSIneoH DNA with *H. saimiri* virion DNA (M-DNA)

Figure 2:
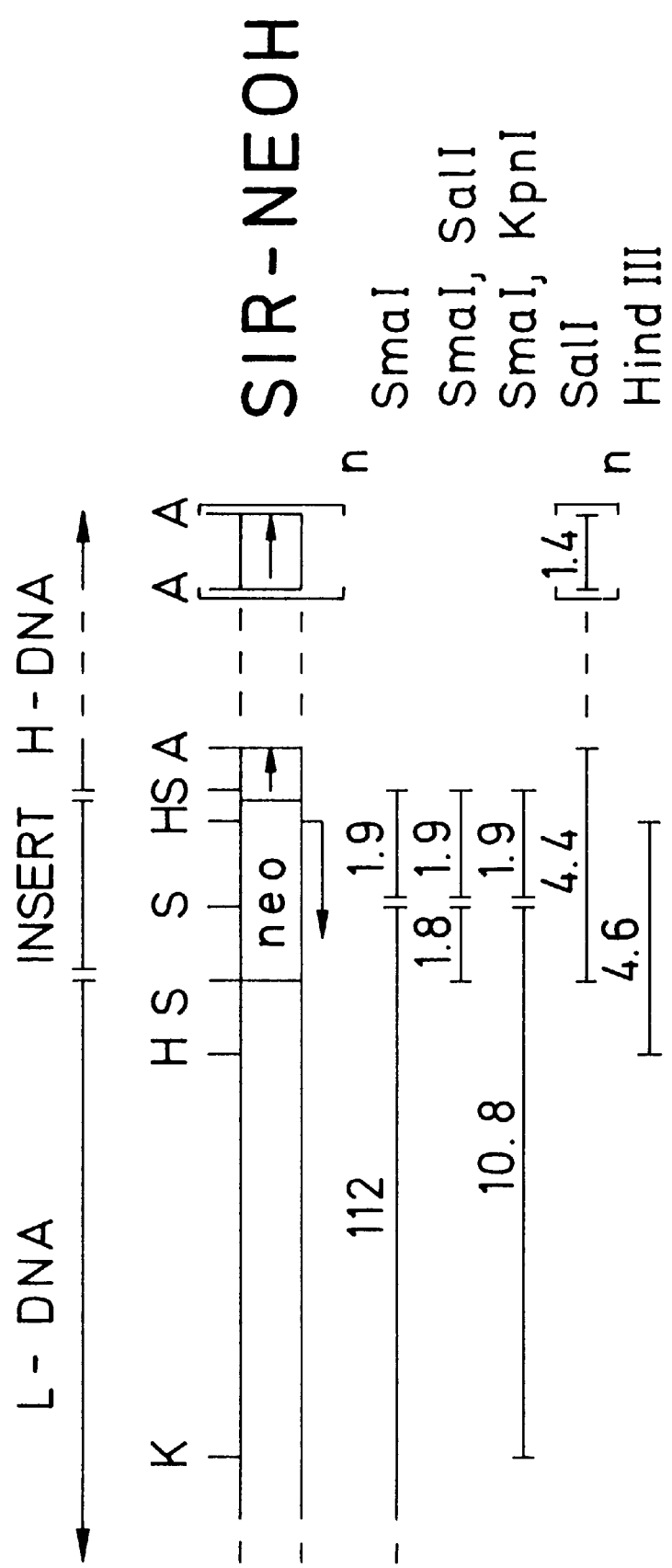
Figure 3:
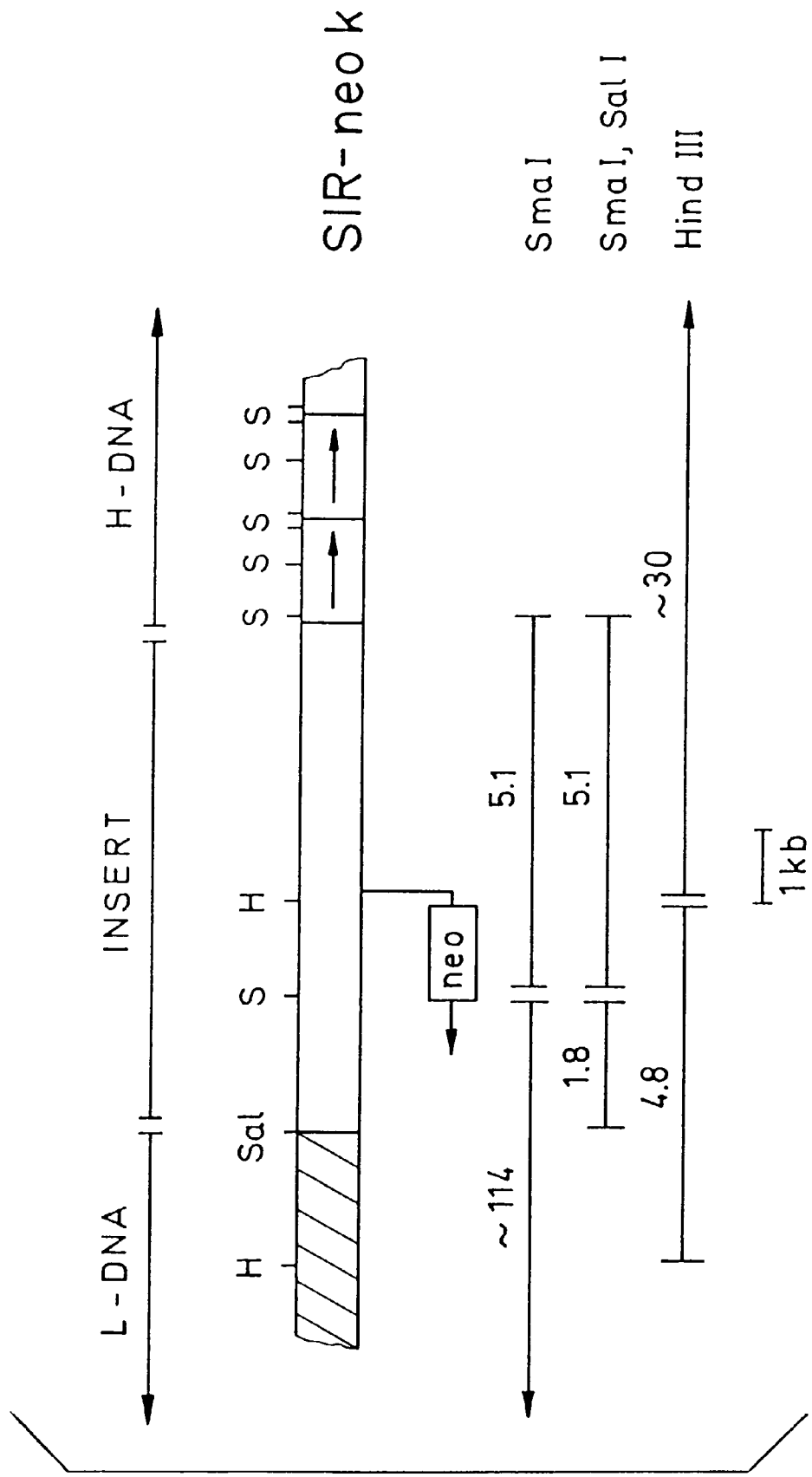

0.2 $\mu$g to 0.4 $\mu$g of M-DNA purified by CsCl density gradients (B. Fleckenstein et al. (1975) J. Virol. 15, 398–406) was mixed with 2 $\mu$g to 4 $\mu$g of pSIneoH linearized by KpnI and transfected into an owl monkey kidney cell line (OMK—637, ATCC CRL 1556) by the calcium phosphate precipitation method (F.L. Graham and J. van der Eg (1973) J. Virol. 52, 456–467), carrying out a 20% w/v glycerol shock after 4 hours. Cytopathic effects were first detectable after about 6 to 10 days and, after a further two weeks, the cells were completely lysed. Owing to the high spontaneous recombination rate, as a rule recombinant *H. saimiri* were obtained without selection pressure. Where the number of recombinants is lower, success is achieved under selection pressure after the transfection, in which case the recombinant yield increases to up to 80%. Restriction analysis with SalI and SmaI in conjunction with Southern blots showed that about two thirds of the virus plaques contain a complete neo gene. Six of 9 clones had the neo gene or pSIneoH DNA inserted between the H-DNA repetition units, and two clones had the neo sequence inserted in the H/L junction site. The characteristics of one of these clones, *H. saimiri* SIRneoH14, are shown in the form of its gene map in FIG. 2. All *H. saimiri* SIRneoH recombinants express the neo gene and can be selected in suitable cells, for example Sg 021, after they have been infected with virus from the abovementioned cotransfection. Sg 021 cells are an IL-2-dependent marmoset T cell line which can be persistently infected with *H. saimiri* (R. C. Desrosiers et al., (1985) Mol.

Cell. Biol. 5, 2796–2803). In this case, the gene dose of the neo gene increases with increasing G 418 concentration from about 40 at 100 μg/ml G 418 to about 140 at 750 μg/ml G 418.

Recombinant "neo virus" is in turn obtained from the Sg 021 cells by cocultivation with OMK cells.

EXAMPLE 3

Cotransfection of pSIneo DNA with *H. saimiri* virion DNA

In order to increase the yield of recombinants which insert the neo gene into the H/L junction site, cotransfection was carried out in principle as in Example 2, but in this case with linearized pSIneo DNA. The viruses *H. saimiri* SIRneoK resulting from this transfection had the neo sequence within the pSIneo DNA inserted between the L/H junction site, as shown in FIG. 3. Expression and amplification of the neo gene, as well as production of infectious recombinant virus, was carried out as described in Example 2.

EXAMPLE 4

Persistent infection of human T cells with recombinant *H. saimiri* virus

The permanently growing human T cell line JURKAT (U. Schneider et al. (1977) Int. J. Cancer 19, 626; ATCC CRL 8163) was infected with *H. saimiri* SIRneoH14 and cultivated with increasing concentrations of geneticin in RPMI 1640 medium containing 10% fetal calf serum. The neo gene was present in the persistently infected JURKAT cells in a gene dose of about 100 per cell, which corresponds to the number of *H. saimiri* SIRneoH14 genomes per cell. The viral DNA is not integrated into the cellular genome but is present as episomal DNA. About 100 copies of the recombinant virus were present per cell.

BRIEF DESCRIPTION OF THE DRAWINGS

FIG. 1

1 designates the plasmid PSV2 neo
2 designates the plasmid PSV2 neo CS
3 designates the plasmid pWD 11
4 designates the plasmid pFG 24
C represents ClaI; E represents EcoRI; K represents KpnI
S represents SalI; Sm represents SmaI
T represents TaqI.

The shaded regions designate the *H. saimiri* DNA portion (terminal KpnI-SmaI fragment of the L-DNA), and black triangles designate the H-DNA repeat units.

FIG. 2

The right H-/L-DNA junction of SIR-NEOH 14 is depicted. H represents HindIII; K represents KpnI; S represents Sma I; Sa represents SalI; A represents the cleavage site of the viral concatemers. The numbers denote the length of the DNA in kb.

FIG. 3

FIG. 3 depicts the neo sequence within the pSIneo DNA inserted between the L/H junction site.

We claim:

1. A *Herpesvirus saimiri* vector, wherein one or more foreign genes are inserted in the right or left junction region of the L- and H-DNA.

2. The *Herpesvirus saimiri* vector of in claim 1 wherein a selection gene is inserted in the right or left junction region of the L- and H-DNA.

3. The vector of claim 1, wherein the a gene encoding neo is inserted.

4. The vector of claim 1, wherein said vector is derived from a non-oncogenic *Herpesvirus saimiri* variant.

5. A process for the preparation of the vector of claim 1, said process comprising ligating a selection gene and/or one or more foreign genes into the right or left junction region of the L- and H-DNA.

6. A method of use of the vector, of claim 1, for the expression of foreign genes in human T cells, said method comprising transforming human T cells with said vector; and expressing the foreign genes contained within said vector.

7. A process for the expression of foreign genes in human T cells, which comprises said cells being transformed by the vector of claim 1 and expressing the foreign gene contained within said vector.

8. The vector of claim 2, wherein the a gene encoding neo is inserted.

9. The vector of claim 2, wherein said vector is derived from a non-oncogenic *Herpesvirus saimiri* variant.

10. A process for the preparation of the vector of claim 2, said process comprising ligating a selection gene and/or one or more foreign genes into the right or left junction region of the L- and H-DNA.

11. A method of use of the vector, of claim 2, for the expression of foreign genes in human T cells, said method comprising transforming human T cells with said vector; and expressing the foreign genes contained within said vector.

12. A process for the expression of foreign genes in human T cells, which comprises said cells being transformed by the vector of claim 2 and expressing the foreign gene contained within said vector.

13. The process of claim 5, further comprising the ligation being carried out by recombination.

14. The process of claim 10, further comprising the ligation being carried out by recombination.

* * * * *